United States Patent [19]

Wu et al.

[11] 4,250,303
[45] Feb. 10, 1981

[54] N-BENZYL ANTHRACYCLINES

[75] Inventors: Helen Y. Wu, San Jose; Thomas H. Smith, San Carlos, both of Calif.; David W. Henry, Chapel Hill, N.C.

[73] Assignee: SRI International, Menlo Park, Calif.

[21] Appl. No.: 69,560

[22] Filed: Aug. 24, 1979

Related U.S. Application Data

[63] Continuation-in-part of Ser. No. 947,874, Oct. 2, 1978, Pat. No. 4,177,264, which is a continuation-in-part of Ser. No. 842,787, Oct. 17, 1977, abandoned.

[51] Int. Cl.$^3$ ............................................. C07H 15/24
[52] U.S. Cl. .................................. 536/17 A; 424/180
[58] Field of Search ...................... 536/17 A; 424/180

[56] References Cited

U.S. PATENT DOCUMENTS 3,803,124  4/1974  Arcamone et al. ................ 536/17 A

*Primary Examiner*—Johnnie R. Brown
*Attorney, Agent, or Firm*—Donovan J. De Witt

[57] ABSTRACT

N-Benzyl and N,N-dibenzyl derivatives of the anthracycline compounds adriamycin and daunomycin, said derivatives having anticancer properties and being active against leukemia P-388 in mice, for example. The N,N-dibenzyl derivatives have the unique quality of exhibiting a loss of DNA-binding properties.

1 Claim, No Drawings

N-BENZYL ANTHRACYCLINES

ORIGIN OF INVENTION

The invention described herein was made in the course of or under a contract with the U.S. Department of Health, Education, and Welfare.

This application is a continuation-in-part of Ser. No. 947,874, filed Oct. 2, 1978, now U.S. Pat. No. 4,177,264, which in turn is a continuation-in-part of Ser. No. 842,787 filed Oct. 17, 1977, now abandoned.

SUMMARY OF INVENTION

The present invention relates to the provision of novel N-benzyl and N,N-dibenzyl derivatives of adriamycin and daunomycin and to compositions containing the same, said derivatives have utility as anticancer chemicals and exhibiting the structure

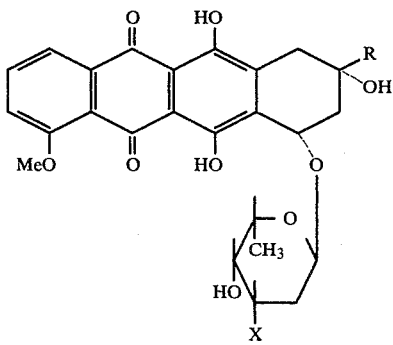

wherein R represents —COCH$_3$, —CHOH—CH$_3$, —COCH$_2$OH or —CHOH—CH$_2$OH and wherein X represents —NHCH$_2$Ph or —N(CH$_2$Ph)$_2$ in which "Ph" represents a phenyl group, and their pharmaceutically acceptable acid addition salts.

For ease of identification, the eight compounds falling within the scope of the present invention are enumerated (I through VIII) in Table I below.

TABLE 1

|  | X = NHCH$_2$Ph | X = N(CH$_2$Ph)$_2$ |
|---|---|---|
| R = COCH$_3$ | I | V |
| R = CHOH—CH$_3$ | II | VI |
| R = COCH$_2$OH | III | VII |
| R = CHOH—CH$_2$OH | IV | VIII |

The preparation of the foregoing compounds is described in detail by the examples. However, it may be noted here that reductive alkylation of daunomycin (IX) with benzaldehyde in the presence of sodium cyanoborohydride for prolonged reaction periods at room temperature produces good yields of the N,N-dibenzyl compound (V), plus the 13-dihydro derivative (VI) as byproduct. With shorter reaction periods, the mono-N-benzyldaunomycin I and II predominate. Either N-benzylation or N,N-dibenzylation can be favored by choosing the stoichiometry. N,N-Dibenzyladriamycin (VII) was similarly obtained by treating adriamycin (X) with benzaldehyde and sodium cyanoborohydride under conditions that gave predominantly mono-N-benzylation, compound (III). Since reductive alkylation is accompanied by ketone reduction, four products (I, II, V, VI) were observed in the benzylation of daunomycin and four more (III, IV, VII, VIII) from the benzylation of adriamycin.

The compounds of the present invention can be prepared either in the free base or acid addition salt form. The salts are soluble in water and aqueous propylene glycol, for example, while the compounds in free base form are soluble in selected organic solvents such as chlorofrom, methylene chloride and ethyl acetate, for example. The salts are thus particularly well adapted for use in antitumor applications since they may be used in aqueous (including saline) solution form. These acid addition salts (prepared here as those of HCl) are preferably the pharmaceutically acceptable, nontoxic addition salts with suitable acids such as those with inorganic acids, for example, hydrochloric, hydrobromic, nitric, sulphuric and phosphoric acids, and with organic acids, such as organic carboxylic acids, for example, glycolic, maleic, hydroxymaleic, malic, tartaric, citric, salicylic acids, and organic sulphonic acids, for example, methanesulphonic and toluene-p-sulphonic acids.

An acid addition salt can be converted into the free compound according to known methods, for example, by treating it with a base, such as with a metal hydroxide or alkoxide, for example, an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example sodium, potassium or calcium carbonate or hydrogen carbonate; with ammonia; or with a hydroxyl ion exchange resin, or with any other suitable reagent.

An acid addition salt may also be converted into another acid addition salt according to known methods; for example, a salt with an inorganic acid may be treated with a metal salt, for example a sodium, barium or silver salt, of an acid in a suitable diluent, in which a resulting inorganic salt is insoluble and is thus removed from the reaction medium. An acid addition salt may also be converted into another acid addition salt by treatment with an anion exchange preparation.

The preparation of each of the foregoing compounds is described in the following examples:

EXAMPLE 1

N-Benzyldaunomycin (I), N-Benzyl-13-dihydrodaunomycin (II) and N,N-Dibenzyldaunomycin (V), and HCl salts Daunomycin.HCl (2.26 g, 4.0 mmol) and benzaldehyde (8.2 mL, 80.0 mmol) were placed in 3:1 acetonitrile/H$_2$O (116 mL) and stirred at 23° for 0.5 hour. NaCNBH$_3$ (0.75 g, 12.0 mmol) was added and stirring was continued for 0.5 hour. The reaction was diluted with H$_2$O (150 mL) and extracted with CHCl$_3$ (3×100 mL). The extracts were combined, washed with H$_2$O (30 mL) and the aqueous phase reextracted with CHCl$_3$ (50 mL). The organic solutions were combined and extracted with cold 0.1 N HOAc (6×100 mL). The extracts were combined, immediately basified with NaHCO$_3$ and extracted with CHCl$_3$ (3×300 mL). The extracts were combined, evaporated and the residue chromatographed (1.3 kg silica gel—50 mm×7 ft dry column—10:1 CHCl$_3$/MeOH) to afford 1.06 g of N-benzyldaunomycin (I) (51%) and 0.17 g of N-benzyl-13-dihydrodaunomycin (II) (7%) as the free bases. The organic solution after the HOAc extraction was dried and evaporated. The residue was chromatographed (560 g silica gel—50 mm×3 ft dry column—10:1 CHCl$_3$/MeOH) to afford 0.18 g (6%) of N,N-dibenzyldaunomycin (V) free base. The HCl salts were prepared by reacting a CHCl$_3$ solution of each compound with an equivalent amount of methanolic HCl followed by precipitation with ether to afford; 1.28 g (49%) of (I); $[\alpha]_D+252°$ (c 0.05 95% EtOH); tlc (10:1 CHCl$_3$/MeOH) R$_f$ 0.60, Anal. calcd for C$_{34}$H$_{35}$NO$_{10}$.HCl.H$_2$O:

|  | C | H | N | Cl |
|---|---|---|---|---|
|  | 60.76 | 5.70 | 2.08 | 5.28 |
| Found: | 60.88 | 5.59 | 1.99 | 5.40; |

0.16 g (6%) of (II); $[\alpha]_D+207°$, (c 0.047, 95% EtOH); tlc (10:1 CHCl$_3$/MeOH) R$_f$ 0.4, Anal. calcd for C$_{34}$H$_{37}$NO$_{10}$.HCl.1.25 H$_2$O:

|  | C | H | N | Cl |
|---|---|---|---|---|
|  | 60.17 | 6.02 | 2.06 | 5.22 |
| Found: | 60.07 | 5.79 | 2.26 | 5.38; | and 0.16 g (5%) of (V); $[\alpha]_D+283°$ (c 0.048, 95% EtOH); tlc (10:1 CHCl$_3$/MeOH) R$_f$ 0.90, Anal. calcd for C$_{41}$H$_{41}$NO$_{10}$.HCl.0.75 H$_2$O:

|  | C | H | N | Cl |
|---|---|---|---|---|
|  | 64.99 | 5.79 | 1.85 | 4.68 |
| Found: | 65.08 | 5.69 | 1.77 | 4.45. |

EXAMPLE 2

N-Benzyladriamycin (III), N,N-Dibenzyladriamycin (VII), and N-Benzyl-13-dihydroadriamycin (IV), and HCl salts.

Adriamycin.HCl (2.90 g, 5.0 mmol) and benzaldehyde (10.5 mL, 100 mmol) were placed in 2:1 acetonitrile/H$_2$O (150 mL) and stirred at 23° for 20 minutes. The solution was added dropwise over 15 minutes to a solution of NaCNBH$_3$ (0.94 g, 15.0 mmol) and benzaldehyde (10.5 mL) in 2:1 acetonitrile/H$_2$O (60 mL). Stirring was continued for 30 minutes and the reaction was diluted with H$_2$O (150 mL) and extracted with CHCl$_3$(4×100 mL). The extracts were combined, washed with saturated NaCl (2×100 mL), dried and evaporated. The residue was chromatographed (1.3 kg silica gel—50 mm×7 ft dry column—40:10:1 CHCl$_3$/MeOH/H$_2$O) to afford 0.10 g (3%) N,N-dibenzyladriamycin (VII), and 1.02 g (30%) of N-benzyladriamycin (III), and 1.20 g (38%) of N-benzyl-13-dihydroadriamycin (IV) as the free bases. Eluting after (VII) was a small amount of material, never completely purified, but tentatively identified as N,N-dibenzyl-13-dihydroadriamycin (VIII). (See Example 4 for a larger preparation of (VIII).) These were converted to the HCl salts by the procedure described in the previous example to afford 0.07 g (2%) of (VII); $[\alpha]_D+275°$ (c 0.051, 85% EtOH); tlc (10:1 CHCl$_3$/MeOH) R$_f$ 0.85, Anal. calcd for C$_{41}$H$_{41}$NO$_{11}$.HCl.0.6 H$_2$O:

|  | C | H | N | Cl |
|---|---|---|---|---|
|  | 63.86 | 5.64 | 1.81 | 4.59 |
| Found: | 63.88 | 5.57 | 1.83 | 4.45; |

0.90 g (28%) of (III); $[\alpha]_D+209°$ (c. 0.048, 95% EtOH); tlc (10:1 CHCl$_3$/MeOH) R$_f$ 0.55, Anal. calcd for C$_{34}$H$_{35}$NO$_{11}$.HCl.H$_2$O:

|  | C | H | N | Cl |
|---|---|---|---|---|
|  | 59.34 | 5.56 | 2.03 | 5.15 |
| Found: | 59.46 | 5.40 | 2.01 | 5.37; | and 1.00 g (30%) of (IV); $[\alpha]_D+204°$ (c 0.050, 95% EtOH); tlc (10:1 CHCl$_3$/MeOH) R$_f$ 0.25, Anal. calcd for C$_{34}$H$_{37}$NO$_{11}$.HCl.0.8 H$_2$O:

|  | C | H | N | Cl |
|---|---|---|---|---|
|  | 59.48 | 5.87 | 2.04 | 5.16 |
| Found: | 59.43 | 5.81 | 2.05 | 5.40. |

EXAMPLE 3

N,N-Dibenzyldaunomycin (V), N,N-Dibenzyl-13-dihydrodaunomycin (VI), N-Benzyldaunomycin (I) and N-Benzyl-13-dihydrodaunomycin (II), and HCl salts.

Daunomycin.HCl (2.54 g, 4.5 mmol) and benzaldehyde (9.2 mL, 90.0 mmol) were placed in 2:1 acetonitrile/H$_2$O (90 mL) and stirred at 23° for 20 minutes. The solution was added dropwise over 20 minutes to a stirred solution of NaCNBH$_3$ (0.57 g, 9.0 mmol) in acetonitrile (20 mL) and stirring was continued for 14 days. The reaction was diluted with H$_2$O (150 mL) and extracted with CHCl$_3$ (5×100 mL). The extracts were combined, washed with H$_2$O (100 mL) and the aqueous layer extracted with CHCl$_3$ (50 mL). The organic solutions were combined, dried and evaporated and residue chromatographed (190 g silica gel—2.8×64 mm column—CHCl$_3$ to 9:1 CHCl$_3$/MeOH) to afford in order of elution 1.19 g (38%) of (V), 0.41 g (13%) of N,N-dibenzyl-13-dihydrodaunomycin (VI), 0.30 g (11%) of (I) and 0.10 g (4%) of (II) as the free bases. These were converted to HCl salts by the above procedure to afford 1.20 g (35%) of (V) and 0.37 (11%) of (VI); $[\alpha]_D+247°$ (c 0.049, 95% EtOH), tlc (10:1 CHCl$_3$/MeOH) R$_f$ 0.85.

Anal. calcd for C$_{41}$H$_{43}$NO$_{10}$.HCl.1.5 H$_2$O;

|  | C | H | N | Cl |  |
|---|---|---|---|---|---|
|  | 63.68 | 6.13 | 1.81 | 4.58 |  |
| Found: | 63.66 | 5.75 | 1.78 | 4.86; | and |

0.23 g (8%) of (I) and 0.07 g (2%) of (II), as HCl salts.

EXAMPLE 4

N,N-Dibenzyl-13-dihydroadriamycin (VIII)

To a stirred suspension of 1.85 g (3 mmoles) of adriamycin .HCl in 200 ml CH$_3$CN was added 80 ml of H$_2$O and then 12.8 ml (120 mmoles) of φCHO. The reaction mixture was stirred at room temperature for 30 minutes. To the stirred solution was added 950 mg (15 mmoles) of NaCNBH$_3$ as a solid. The reaction mixture was stirred at room temperature for 5 days. Some ppt.

formed. A total of 400 ml of 2:1 CH₃CN/H₂O was added to dissolve the ppt. The reaction mixture was then stirred at room temperature for 9 additional days. The mixture was then diluted with 300 ml of H₂O and extracted 7× with 400 ml of 4:1 CHCl₃/MeOH. The combined MeOHCHCl₃ extracts were washed with 100 ml H₂O (water layer was back extracted 2× with 50 ml 2:1 CHCl₃/MeOH). The combined organic extracts were dried over anhydrous Na₂SO₄ and filtered and evaporated to yield 500 mg of the free base of VIII.

This free base was converted to its HCl salt by reaction with an equivalent amount of HCl in MeOH and precipitated with CHCl₃ and anhydrous ether, filtered, and dried under vacuum over night.

Yield of VIII salt was 400 mg, approximately 16%.

| Elemental analysis | C | H | N | Cl$^{\ominus}$ |
|---|---|---|---|---|
| Calc. for $C_{41}H_{43}NO_{11}$ · HCl · 1.4 H₂O | 62.54 | 5.98 | 1.78 | 4.50 |
| Found: | 62.52 | 5.72 | 1.98 | 4.8 |

The compounds of this invention, including the salts thereof, can be administered by any available route, including oral and parenteral (intravenous, intraperitoneal, subcutaneous, and intramuscular) administration. The amount administered is sufficient to ameliorate the leukemia or other type of cancer against which the compounds hereof may prove to be effective. For example, in the treatment of lower test animals, a dosage of a compound of the present invention within the range from about 0.1 mg/kg to about 500 mg/kg per day should be sufficient to ameliorate leukemia. The upper dosage limit is that imposed by toxic side effects and can be determined by trial and error for the animal to be treated.

To facilitate administration, the compounds of this invention, including the salts thereof, can be provided in composition form, and preferably in dosage unit form. While any compound selected can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the anti-cancer agent. Exemplary diluents and carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan, monolaurate, methyl- and propyl-hydroxybenzoate, talc or magnesium stearate.

For convenience in handling, the compounds hereof and the carrier or diluent can be enclosed or encapsulated in a capsule, sachet, cachet, gelatin, paper or other container, especially when intended for use in dosage units. The dosage units can for example take the form of tablets, capsules, suppositories or cachets.

The following examples illustrate various forms of dosage units in which the HCl salt of compound V can be prepared.

EXAMPLE 5

| Tablet formulation | Mg/tablet |
|---|---|
| Compound V | 15 |
| Lactose | 86 |
| Cornstarch (dried) | 45.5 |
| Gelatin | 2.5 |
| Magnesium stearate | 1.0 |

Compound V is powdered and passed through a mesh sieve and well mixed with the lactose and 30 mg of the cornstarch, both passed through a sieve.

The mixed powders are massed with a warm gelatin solution, prepared by stirring the gelatin in water and heating to form a 10% w/w solution. The mass is granulated by passing through a sieve, and the moist granules dried at 40° C.

The dried granules are regranulated by passing through a sieve and the balance of the starch and the magnesium stearate is added and thoroughly mixed.

The granules are compressed to produce tablets each weighing 150 mg.

EXAMPLE 6

| Tablet formulation | Mg/tablet |
|---|---|
| Compound V | 100 |
| Lactose | 39 |
| Cornstarch (dried) | 80 |
| Gelatin | 4.0 |
| Magnesium stearate | 2.0 |

The method of preparation is identical with that of Example 4 except that 60 mg of starch is used in the granulation process and 20 mg during tableting.

EXAMPLE 7

| Capsule formulation | Mg/capsule |
|---|---|
| Compound V | 250 |
| Lactose | 150 |

Compound V and lactose are passed through a sieve and the powders well mixed together before filling into hard gelatin capsules of suitable size, so that each capsule contains 400 mg of mixed powders.

EXAMPLE 8

| Suppositories | Mg/suppository |
|---|---|
| Compound V | 50 |
| Oil of Theobroma | 950 |

Compound V is powdered and passed through a sieve and triturated with molten oil of theobroma at 45° C. to form a smooth suspension.

The mixture is well stirred and poured into molds, each of nominal 1 g capacity, to produce suppositories.

EXAMPLE 9

| Cachets | Mg/cachet |
|---|---|
| Compound V | 100 |
| Lactose | 400 |

Compound V is passed through a mesh sieve, mixed with lactose previously sieved and fitted into cachets of suitable size so that each contains 500 mg.

EXAMPLE 10

| Intramuscular injection (sterile suspension in aqueous vehicle) | Mg |
|---|---|
| Compound V | 10 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

EXAMPLE 11

| Intraperitoneal, intravenous or subcutaneous injection (sterile solution in aqueous carrier system) | Mg |
|---|---|
| Compound V, hydrochloric acid addition salt | 15 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

The other compounds of this invention could be prepared in dosage unit form in the same general fashion as that described above for compound V.

BIOLOGICAL TESTS

Biological screening results obtained in both in vitro and in vivo tests are shown in Table 2 below. It will be seen that every compound was active against leukemia P388 in mice. The in vitro results are surprising and appear to be highly significant in that there is an abrupt and unexpected loss of DNA-binding properties in going from N-benzyl to N,N-dibenzyl compounds. $\Delta T_m$ is the most direct measure of DNA-binding but the inhibition of nucleic acid synthesis is also lost. Most of the anthracyclines bind to DNA, presumably by an intercalation mechanism and are mutagenic. In these N,N-dibenzyl compounds the anti-tumor activity in the mouse screen is retained but the DNA-binding properties are lost. This suggests the N,N-dibenzyl compounds may be useful and effective anti-cancer agents, but may act by a different mechanism from most of the other anthracyclines, and thus may avoid the serious cardiotoxic side effects common to the anthracyclines now in use.

The compound referred to herein as daunomycin (IX) is otherwise known as daunorubicin or rubidomycin.

TABLE 2

IN VITRO AND IN VIVO TESTS OF N-BENZYL ANTHRACYCLINES

| Compound No. | NSC No.[a] | $\Delta T_m(°C.)$[b] | L1210 Cells[c] Inhib of Synth DNA ED$_{50}$, μM | RNA ED$_{50}$, μM | Highest Mean T/C vs P388 in Mice[d] qd 1-9 % T/C (dose, mg/kg) | q4d 5,9,13 % T/C (dose, mg/kg) |
|---|---|---|---|---|---|---|
| Parents | | | | | | |
| IX | 82151 Daunomycin | 11.2 | 1.0 | 0.3 | 167 (0.5) | 134 (8) |
| X | 123127 Adriamycin | 13.4 | 1.5 | 0.67 | 193 (1.0) | 157 (8) |
| N-Benzyl | | | | | | |
| I | 268241 Dnm, N-benzyl | 10.2 | 1.6 | 0.17 | 187 (6.25) | 226 (18.8) |
| II | 268240 Dnm, N-benzyl, 13-diH | 6.25 | 1.7 | 0.32 | 226 (6.25) | — |
| III | 269433 Adm, N-benzyl | 11.3 | 0.65 | 0.09 | 224 (6.25) | 200 (18.8) |
| IV | 269434 Adm, N-benzyl, 13-diH | 7.6 | 1.4 | 0.29 | 196 (1.56) | 143 (37.5) |
| N,N-Dibenzyl | | | | | | |
| V | 268242 Dnm, N,N-dibenzyl | 1.35 | >100 | 10 | 259 (25) | 227 (37.5) |
| VI | 278170 Dnm, N,N-dibenzyl, 13-diH | 0.6 | 220 (susp) | 7.6 | 229 (40) | 233 (50) |
| VII | 269435 Adm, N,N-dibenzyl | −1.2 | 110 | 4.8 | 175 (6.25) | — |
| VIII | 316162 Adm, N,N-dibenzyl, 13-diH | insol | 160 | 8.0 | — | 209 (100) |

[a]NSC accession number of the National Cancer Institute.
[b]$\Delta T_m$ values represent the difference in temperature between that at which the DNA denatures (or melts) without the drug and that at which denaturing occurs in the presence of the drug; $\Delta T_m$ values around 1° suggest weak binding, if any, to isolated helical DNA; values ≧5° suggest a significant degree of binding.
[c]Assay described in G. Tong, W. W. Lee, D. R. Black and D. W. Henry, J. Med. Chem., 19, 395 (1976).
[d]Ip P388 murine leukemia treated ip on QD1-9 and Q4D 5,9,13 schedules according to standard NCI protocols. Assay described in R. I. Geran, N. H. Greenberg, M. M. MacDonald, A. M. Schumacker and B. J. Abbott, Cancer Chemother. Rep., Part 3, 3, (No. 2), 9 (1972). Protocol 1,200. T/C = ratio of survival time of treated mice to that of untreated controls times 100. Untreated controls survive about 9 days. For Dnm and Adm, % T/C values are means from several dozen tests, with standard deviation up to ±40. For the N-benzyl compounds, % T/C values are means from all the tests (1 to 3) so far, as the optimum dose.

What is claimed is:

1. The compound which is N,N-dibenzyl-13-dihydroadriamycin, together with its pharmaceutically acceptable acid addition salts.

* * * * *